(12) United States Patent
Tiba et al.

(10) Patent No.: US 6,673,958 B2
(45) Date of Patent: Jan. 6, 2004

(54) MULTIFUNCTIONAL DENTIN BONDING AGENT

(75) Inventors: Amer Tiba, Schaumburg, IL (US);
Martin Hamer, Skokie, IL (US);
Byoung I. Suh, Oakbrook, IL (US)

(73) Assignee: Bisco, Inc., Schaumburg, IL (US)

( * ) Notice: Subject to any disclaimer, the term of this patent is extended or adjusted under 35 U.S.C. 154(b) by 30 days.

(21) Appl. No.: 10/071,641

(22) Filed: Feb. 7, 2002

(65) Prior Publication Data

US 2003/0175659 A1 Sep. 18, 2003

(51) Int. Cl.[7] .......................... C09K 3/80; C07C 69/76; A61C 5/00; C08L 33/06; C08L 6/08
(52) U.S. Cl. ...................... 560/76; 206/63.5; 433/222.1; 433/228.1; 523/116; 524/559; 524/560; 106/35
(58) Field of Search .................. 523/115, 118, 523/116; 524/117, 118, 547, 559, 560; 560/76, 356, 770; 526/318.1, 326, 277, 278; 433/318.1, 228.1; 206/63.5; 106/35

(56) References Cited

U.S. PATENT DOCUMENTS

| | | | |
|---|---|---|---|
| 4,437,836 A | 3/1984 | Schmitz-Josten et al. | ... 433/199 |
| 4,439,380 A | 3/1984 | Michl et al. | .................. 264/16 |
| 4,816,495 A | 3/1989 | Blackwell et al. | ............ 522/14 |
| 5,348,988 A | 9/1994 | Suh et al. | .................... 523/118 |

Primary Examiner—Alan L. Rotman
Assistant Examiner—Taylor V. Oh
(74) Attorney, Agent, or Firm—Howrey Simon Arnold & White LLP

(57) ABSTRACT

Novel unsaturated esters for use in dentistry as bonding agents are produced by a stepwise reaction of a cyclic dianhydride with a) unsaturated alcohols, b) unsaturated glycidyl ethers, and c) unsaturated isocyanates. The products used as bonding agents have the formula:

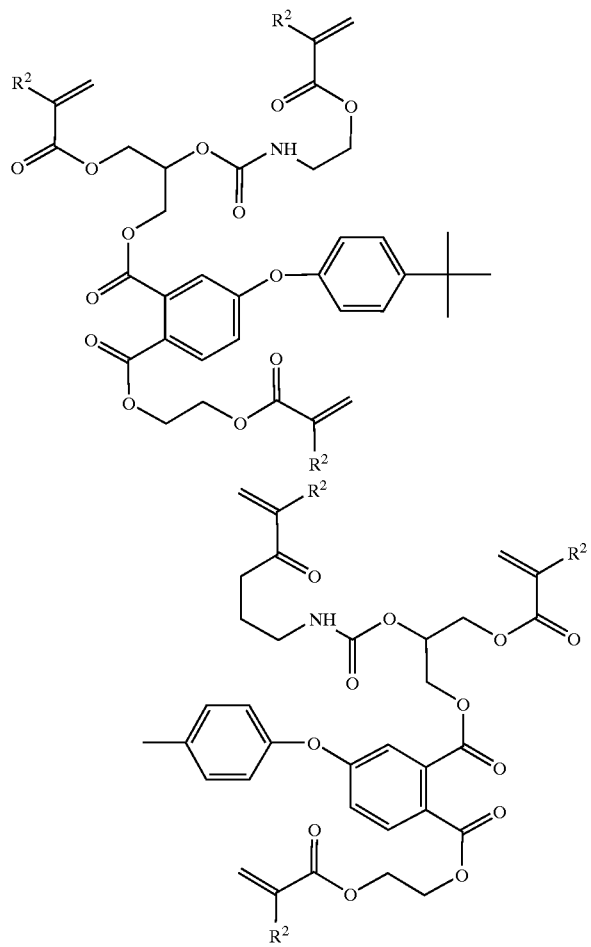

wherein $R^2$ is H or $CH_3$.

9 Claims, No Drawings

MULTIFUNCTIONAL DENTIN BONDING AGENT

BACKGROUND OF THE INVENTION

The present invention relates generally to a group of novel high molecular weight, multi-acrylate compounds which can be used alone or in conjunction with other compounds and which increase the bonding strength between a dental substrate and a dental composite restorative material, decrease shrinkage in the dental composite material, and which have no toxicity.

BRIEF SUMMARY OF THE INVENTION

In accordance with the invention, there is provided a group of novel high molecular weight, multi-acrylate compounds produced by (a) a reaction of unsaturated alcohols with cyclic acid dianhydrides, (b) subsequent reaction of the product of reaction (a) with unsaturated glycidyl ethers, and (c) subsequent reaction of product of reaction (b) with unsaturated isocyanates.

The dianhydrides, which can be used in the invention, are those having the formula:

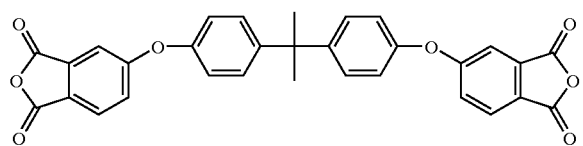

(I)

The unsaturated alcohols useful in the invention are those having the formula:

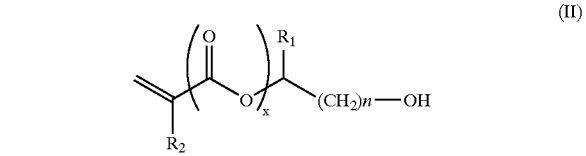

(II)

wherein $R^1$ is H, $CH_3$, or $=CH_2$; $R^2$ is H or $CH_3$; n is 1, 2, 3, or 4; and x is 0 or 1.

The unsaturated glycidyl ethers useful in the invention are those having the formula:

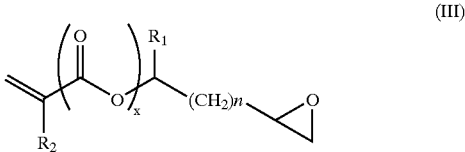

(III)

wherein $R^1$ is H, $CH_3$, or $=CH_2$, $R^2$ is H or $CH_3$; n is 1, 2, 3, or 4; and x is 0 or 1.

The unsaturated isocyanates useful in the invention are those having the formula:

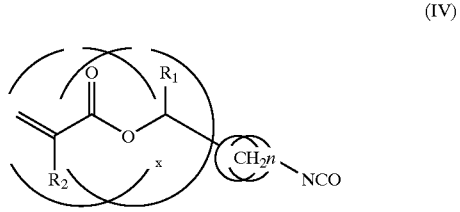

(IV)

wherein $R^1$ is H, $CH_3$, or $=CH_2$; $R^2$ is H or $CH_3$; n is 1, 2, 3, or 4; and x is 0 or 1.

The reaction product produced in this manner is used in accordance with the invention in conjunction with other compounds such as a dentin conditioner or other components of a dental composite material. These materials are applied in solution to an area in which a bond is desired. The bond is usually completed by use with a self-curing initiator or a light cure system.

DETAILED DESCRIPTION OF THE INVENTION

Presently preferred high molecular weight, multifunctional compounds of the present invention are, in general, symmetrical compounds having a polyaromatic nucleus substituted with six acrylate groups. Representative of such preferred high molecular weight, multifunctional compounds of the present invention are those having the following structure:

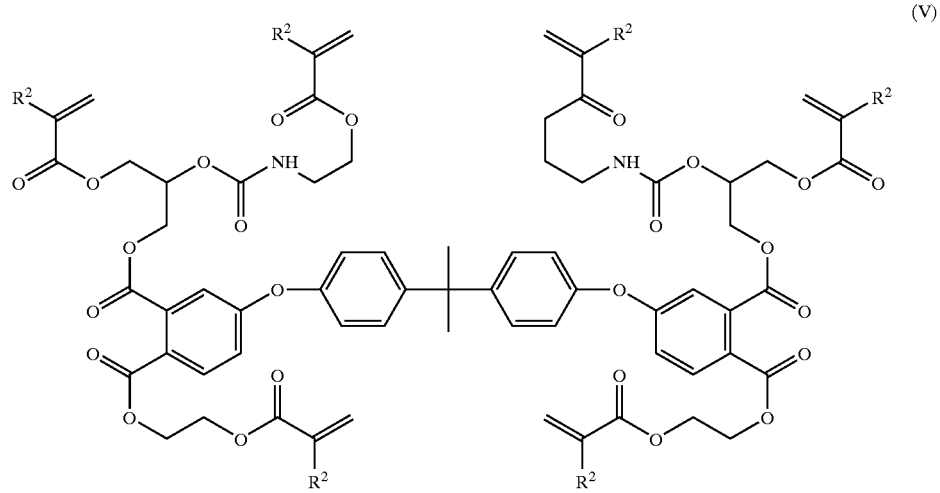

(V)

wherein $R^2$ is H or $CH_3$.

The novel high molecular weight, multi-acrylate compounds are produced by (a) a reaction of unsaturated alcohols with cyclic dianhydrides, (b) subsequent reaction of the product of reaction (a) with unsaturated glycidyl ethers, and (c) subsequent reaction of product of reaction (b) with unsaturated isocyanates.

Presently preferred cyclic dianhydrides useful in the invention are, in general, symmetrical compounds having an aromatic nucleus substituted with four carboxylic acid groups from which two moles of water have been removed to form two cyclic anhydride groupings. Representative of such preferred cyclic dianhydrides, which can be used in the invention, are those having the following structure:

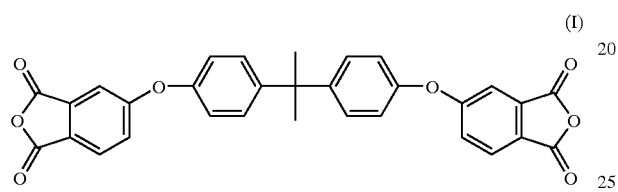
(I)

This compound is produced by General Electric Co. under the name Bisphenol A Dianhydride and may be purchased from the Aldrich Chemical Co. under the name of 4,4'-(4, 4'-isopropylidenediphenoxy)bis(phthalic anhydride). For producing the novel bonding agent components in accordance with the invention, the cyclic dianhydrides as described above are permitted to react in the presence of a small amount of a tertiary amine such as triethylamine, with preferably at least two molar equivalents of an unsaturated alcohol having the formula II.

The preferred unsaturated alcohols used in making the components of the invention are hydroxyethyl methacrylate and hydroxypropyl methacrylate. When these alcohols are reacted with suitable anhydrides in accordance with the invention, there is produced a group of preferred compounds having the formula:

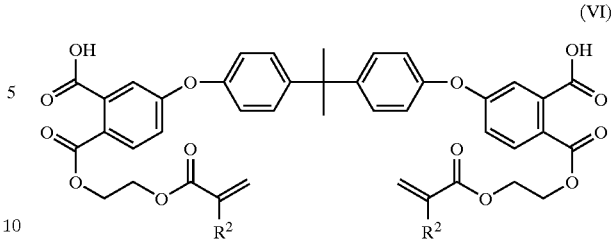
(VI)

wherein $R^2$ is H or $CH_3$.

An example of the preparation of an unsaturated alcohol-cyclic dianhydride product is given in the following reaction, in which symmetrical dianhydride (I) is reacted with two moles of hydroxyethyl methacrylate.

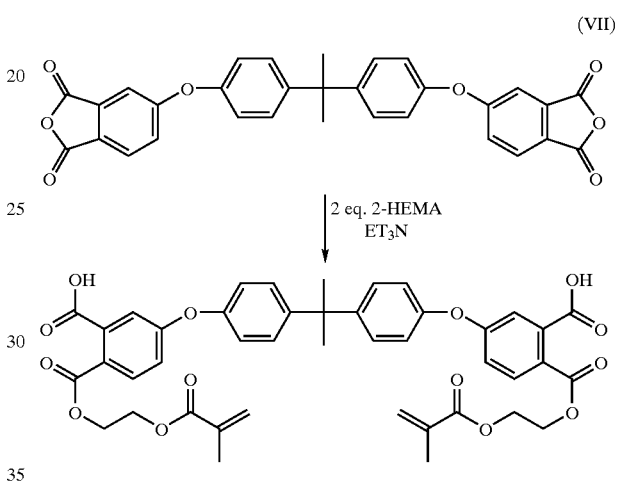
(VII)

The presently preferred product, 4,4'-(4,4'-isopropylidinediphenoxy)bis phthalate methacrylate ester (IDBM, VI) as described above is then permitted to react in the presence of preferably at least two molar equivalents of an unsaturated, glycidyl ether having the formula III.

A preferred unsaturated glycidyl ether used in making the components of the invention is glycidyl methacrylate. When these glycidyl ethers are reacted with products (VI) in accordance with the invention, there is produced a group of preferred compounds having the formula:

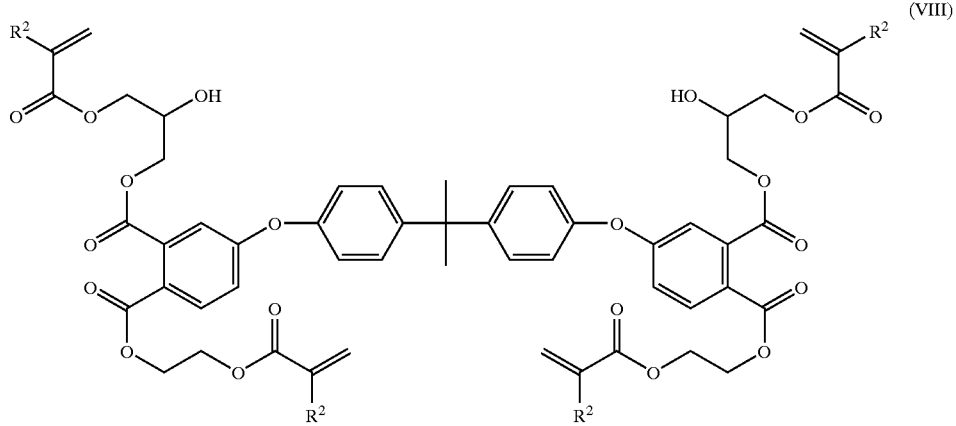
(VIII)

wherein $R^2$ is H or $CH_3$.

An example of the preparation of an unsaturated glycidyl ether-benzoate product is given in the following reaction, in which symmetrical benzoate (VII) is reacted with two moles of glycidyl methacrylate.

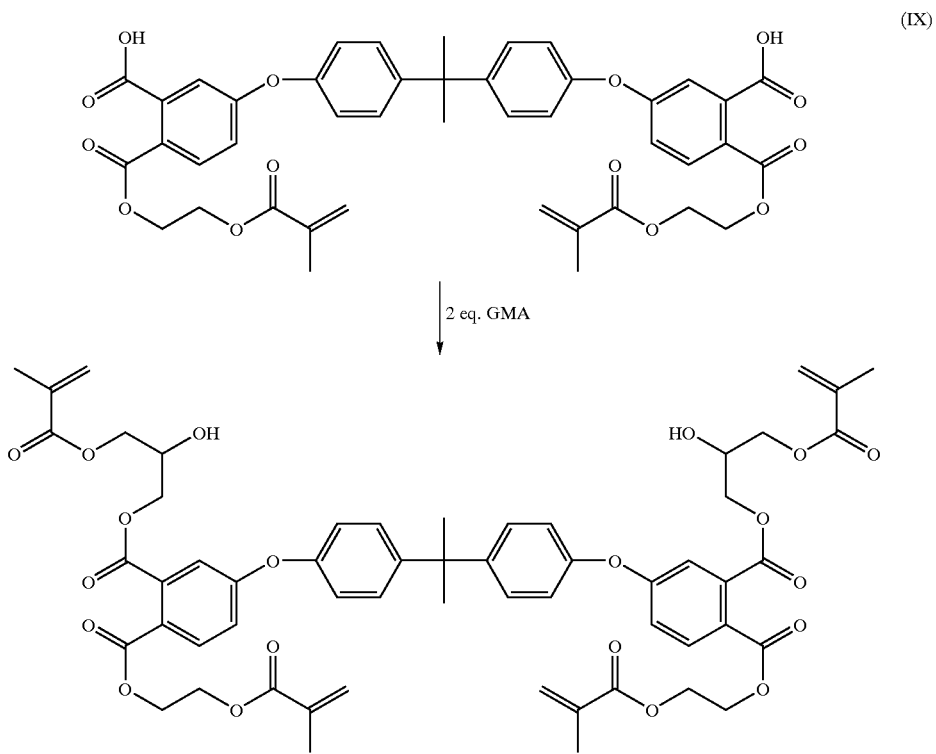

The products (VIII) as described above are permitted to react in the presence of a small amount of a DBTDL (Dibutyltin dilurate) in dichloromethane, with preferably at least two molar equivalents of an unsaturated isocyanate having the formula IV.

A presently preferred unsaturated isocyanate used in making the components of the invention is isocyanoethyl methacrylate. When these isocyanates are reacted with products (VIII) in accordance with the invention, there is produced a group of preferred compounds having the formula:

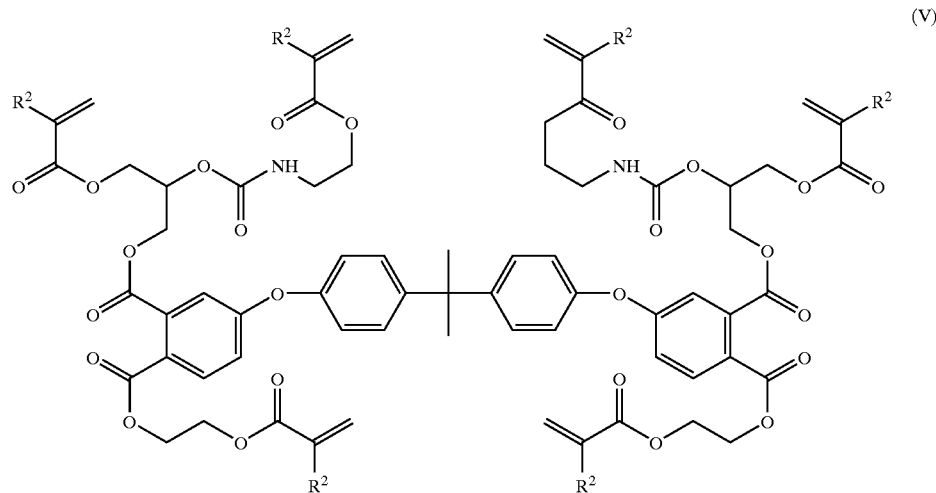

wherein $R^2$ is H or $CH_3$.

An example of the preparation of an unsaturated isocyanate-diester product is given in the following reaction, in which symmetrical diester (VIII) is reacted with two moles of isocyanoethyl methacrylate.

to about 60 weight percent of the total composition. Presently more preferred amounts are in the range of about 5 to about 20 weight percent of the composition.

Preferred fillers according to the present invention include one or more well-known sub-micron size fillers. For

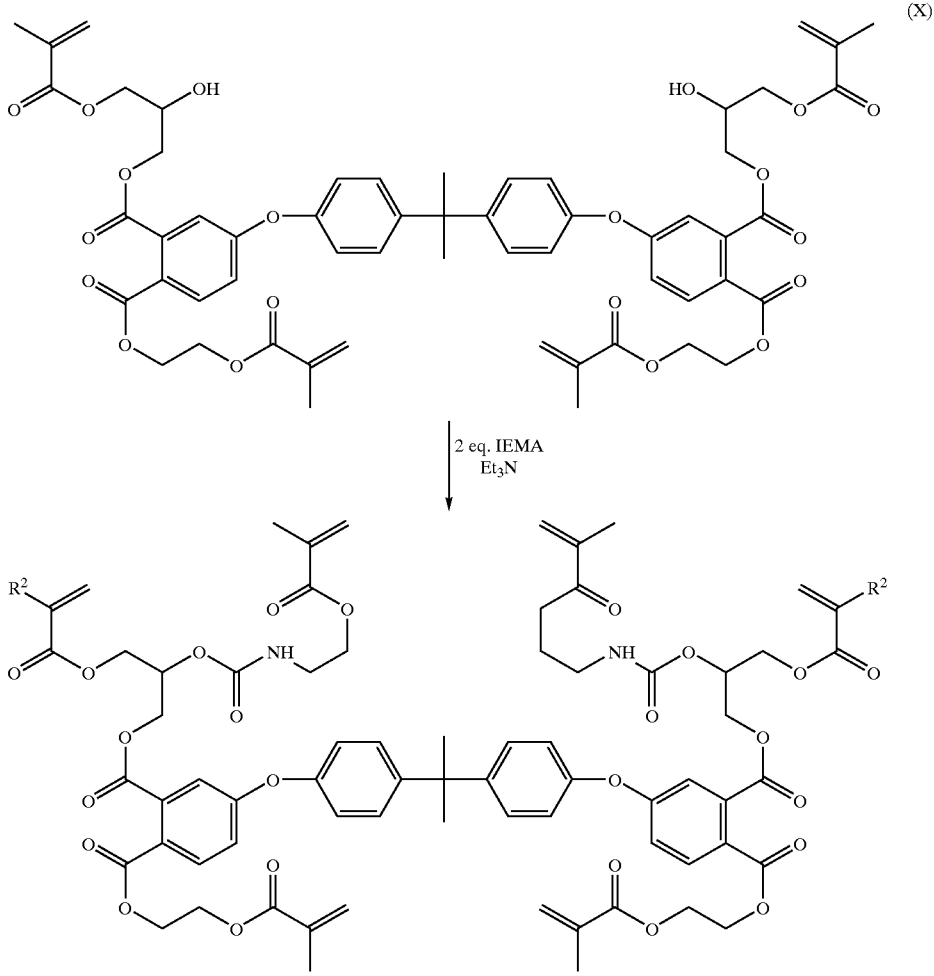

The high molecular weight, multifunctional product (V) illustrated in the above reaction may be one component of a novel dental bonding composition in accordance with the invention. The novel dental bonding compositions of the present invention and methods for their use have particular application in the field of restorative dentistry. Preferred compositions according to the present invention comprise a hexafunctional compound V, a filler portion, a polymerization catalyst portion comprising a polymerization compound or system. Optionally, the compositions may also include an additional multifunctional and/or monofunctional comonomer portion, antimicrobial agents, opaquifiers, fluoride-release agents, colorants and other components, which impart desirable properties to the composition. Such additional agents may be incorporated into one or more of the monomer, comonomer or filler portions of the compositions, or may be added in small amounts to the composition during formulation. Hexafunctional compounds V are used to build up a better cross-linking structure in the polymer matrix. This structure plays a very important role in the mechanical properties of the dental materials.

Presently preferred amounts of hexafunctional compound V in compositions of the present invention are from about 3 example, sub-micron size fillers are silanated oxides of aluminum, zirconium and silicon, silicate glasses, and barium or strontium glasses. The use of sub-micron size fillers is presently preferred to minimize surface wear and "plucking" of filler components from the restorative surface, as well as imparting a surface which may be easily polished by the dental professional. Preferred contemplated filler particles have an average size of about 0.03 to about 4 microns. Presently more preferred fillers have an average particle size of about 0.04 to about 20 microns. Presently more preferred fillers are of a micron or submicron average particle size of about 0.05 to about 10 microns.

One or more of the aforementioned fillers comprising the filler portion may also include caries inhibiting agents such as slow releasing fluoride agents to help inhibit caries from forming in the adjacent tooth structure. For example, glass ionomer IX 1944 from Ferro Corporation, Cleveland, Ohio, which contains such a slow release fluoride agent, is expected to have utility in the present invention.

The filler or fillers are present at about 75 to about 95 weight percent of the contemplated compositions of the present invention, and are more preferably present at about 80 to about 90 weight percent of the composition. The amount of the filler component is adjusted in view of the other components of the composition and in view of the intended use of the composition, it being well known in the art that higher filler amounts generally impart higher compressive strengths to a composition, but also tend to increase viscosity and decrease flowability of the composition. Presently preferred fillers include silanized barium glass from Ferro Corporation, Cleveland, Ohio, silanized submicron glasses such as OX-50 or Aerosil R972 from DeGussa, Richfield Park, N.J., and porcelain ground (SR) glass such as (RWG) from Ferro Corporation, Cleveland, Ohio.

Optionally, the filler portion is formulated to include appropriate coloring agents in varying amounts to provide the dental professional with a range of colors in the composition, which may be selected for compatibility with the shade of the patient's tooth undergoing restoration. Such coloring or tint agents are well known in the art, and may be included in small amount of about 1 weight percent or less of the total composition. Such fillers can also be selected to be radioopaque. For example, appropriate amounts of radioopaque barium, strontium or zirconium glass may be used as all or part of the filler portion, which can assist the dental professional in his or her posttreatment examination of the patient.

A polymerization catalyst compound, composition or system is also included in the preferred compositions of the present invention. Such polymerization compounds, compositions or systems (hereinafter referred to as "systems") are well known in the art. They generally fall within one of three categories: (1) self-curing chemical systems which initiate polymerization upon admixing two or more compounds; (2) light-initiated polymerization systems; and (3) heat-initiated polymerization systems. A polymerization system employing two or more initiators, i.e. light/self cure or light/heat initiated systems is also contemplated to give the dental professional additional flexibility in the restorative procedures.

Exemplary self-curing systems include traditional free radical polymerization initiators normally used with polymerizable ethylenically unsaturated materials and resins. For example, organic peroxide initiators and amine accelerations such as those disclosed in U.S. Pat. No. 4,816,495, whose disclosure is hereby incorporated by reference, may be used, and, as taught therein, packaged separately from the polymerizable monomer components of the system and admixed with the monomers shortly before application to the tooth or dental appliance.

A light or photo-curing or photosensitive polymerization initiation and curing system is also included in a contemplated light-curable composition of the present invention. A contemplated photo-curing system is activated to harden and cure the composition by irradiation with visible or UV light. For example, visible light of a wavelength of about 400 to about 500 $\mu$m initiates rapid and efficient curing.

A light or photo-curing or photosensitive polymerization initiation and curing system according to preferred embodiments of the present invention include alpha-diketone light-sensitive initiator compounds such as benzophenone or a derivative, or a-diketone such as benzil or camphorquinone (CQ) and CQ derivatives and certain tertiary aromatic amine polymerization accelerator compounds. Preferably, photo-initiator systems according to the invention are sensitive to visible light and possibly into a range of other wavelength light that is not harmful to a patient undergoing a dental procedure. Some compounds that may be suitable ultraviolet light-sensitive initiators are 1,2- diketones, benzophenones, substituted benzophenones, benzoin methyl ether, isopropoxybenzoin, benzoin phenyl ether, and benzoin isobutyl ether. Camphorquinone or a CQ derivative is presently preferred.

Presently preferred CQ or CQ derivatives may be added to the composition of the present invention in concentrations that range from about 0.01 wt. % to about 5 wt. %, more preferably from about 0.05 wt. % to about 2 wt. %, and presently most preferably from about 0.1 wt. % to about 1.0 wt. % of the total composition.

As mentioned above a tertiary amine reductant or its salt is also included. Exemplary tertiary amines include tributylamine, tripropylamine, N-alkyldialkanol amines such as N-methyldiethanolamine, N-propyldiethanolamine, N-ethyldiisopropanolamine and trialkanolamines such as triethanolamine and triisopropanolamine. Further useful tertiary amines are specifically disclosed in U.S. Pat. Nos. 4,439,380 and 4,437,836 and 4,816,495. Ethyl 4-dimethylamino benzoate (EDMAB) is a presently preferred tertiary amine reductant.

Presently preferred concentrations of tertiary aromatic amine compounds of the present invention of the formula identified above are from about 0.01 wt. % to about 10 wt. %, more preferably from about 0.05 wt. % to about 5 wt. % and presently most preferably from about 0.1 wt. % to about 2 wt. % of the total composition. The amount of each component of the photo-initiator system depends in part on the amount of monomer present in the solution whose polymerization is to be catalyzed. Particularly preferred photo-initiator systems include CQ and ethyl 4-dimethylaminobenzoate (EDMAB).

The photo-curing system is present in an amount sufficient to cure the cement to a desired strength preferably within about two minutes upon irradiation with light as above. More preferably, the cure time is less than about one minute, and most preferably about 20 to about 30 seconds. In usual practice, both components of the photo-curing system constitute less than about two percent of the weight of the dental compositions of the present invention, and more preferably less than about one weight percent.

Heat-initiated polymerization systems are also contemplated in the compositions of the present invention. Preferred heat initiators will initiate curing at around 60 to 150 degrees Centigrade, and more preferably about 100 to 130 degrees Centigrade. Such systems include benzoyl peroxide, t-butyl perbenzoate, 1,1-di(tert-butyl)peroxide and other well-known catalysts capable of initiating polymerization of ethylenically unsaturated groups or resins.

As indicated above, it is also contemplated that the polymerization initiator system of the present invention may include two or more initiators in the composition. For example, a combination of a light cure initiator system utilizing CQ alone or in combination with a tertiary amine reductant along with a heat curing agent such as t-butyl perbenzoate is expected to have utility in the present invention. Such multi-initiator systems may have utility in that they may include both a rapid cure initiator (light or heat cure) to impart significant polymerization in the dental office or dental laboratory. For example, a light cure system in combination with a longer time self-cure initiator, which continues to cause further polymerization after the patient leaves the office and further secures the restorative to the tooth structure, is also contemplated.

Such dual cure light/heat systems, as well as their respective single initiator systems, are also desirable in that they may be formulated and packaged in one container or syringe, thereby avoiding the need for mixing by the dental professional before application. For example, as set out in the following examples, such one-component systems exhibit good shelf life of more than a year when stored away from light at room temperature. If self-curing compositions are desired, the self-curing initiator may be packaged in one of two containers separately from the polymerizable components of the composition, with the contents of both containers being admixed shortly before use in the dental office.

In general, a highly loaded composite looks very dry and is very hard to handle. Compositions of the present invention also include suitable monomer(s) containing one or more functional groups capable of polymerization reaction with multifunctional compound V. The monofunctional comonomer acts as a diluent to control or reduce the viscosity of the resin as well as to provide fewer polymerization sites, both of which assist in formulating the composition. The addition of a viscosity controlling monofunctional monomer makes the composition and composites of the present invention as easy to work with as normal hybrid composites. Multifunctional comonomer(s) are selected such that they contain two functional groups, which are capable of undergoing polymerization reactions with the other monomer(s) to help impart good flexure and tensile strength to the composition as well as a relatively high degree of cross-linking throughout the composition. Such monofunctional and multifunctional comonomer(s) are preferably present in amount of from about 2 to about 10 weight percent of the composition. The amount of the comonomer portion in the overall composition is dependent in part on the amount of filler and hexafunctional compound V in the composition and in part on the desired viscosity and flow characteristics of the composition.

Suitable monofunctional and multifunctional monomers may include well-known mono-, di-, tri-, and tetraacrylate and methacrylates such as 2,2-bis[4-(3-methacryloxy-2-hydroxypropoxy)phenyl]-propane (BISGMA), Bisphenol A dimethacrylate (Bis A Dima), ethoxylated Bis A Dima, neopentylglycol dimethacrylate, decanediol-1,10-dimethacrylate, dodecanediol-1,12-dimethacrylate, 1,4-butanediol dimethacrylate, ethyleneglycol dimethacrylate, diethyleneglycol dimethacrylate, triethyleneglycol dimethacrylate (3EGDMA), tetraethyleneglycol dimethacrylate (4EGDMA), polyethyleneglycol dimethacrylate, propyleneglycol dimethacrylate, dipropyleneglycol dimethacrylate, tripropyleneglycol dimethacrylate, tetrapropyleneglycol dimethacrylate, polypropyleneglycol dimethacrylate, hexamethyleneglycol dimethacrylate (HMDA), 2,2-bis(4-methacryloxyphenyl)propane, 2,2-bis(4-methacryloxyethoxyphenyl)propane, 1,2-bis(3-methacryloxy-2-hydroxypropoxy)ethane, CPDM-the reaction product of cyclopentane tetracarboxylic acid dianhydride and 2 moles of hydroxyethyl methacrylate (HEMA), tetrahydrofurfuryl cyclohexene dimethacrylate (TCDM)-the reaction product of Epiclon B-4400 (Dainippon Inc. and Chemicals Inc., Ft. Lee, N.J.) with 2 moles of HEMA, 2,2-bis(4-methacryloxyphenyl)-propane, 2-hydroxy-1,3-dimethacryloxypropane, di-2-methacryloxyethyl-2,2,4-trimethylhexamethylene-dicarbamate (LTDMA), di-2-methacryloxyethylisophorone dicarbamate, and di-2-methacryloxyethyl-2,4- or 2,6-tolylene dicarbamate.

Optionally, one or more of the monomer compounds may include a caries inhibiting agent that helps to prevent or inhibit caries formation in the adjacent tooth structure. For example, the fluoride release monomer disclosed in U.S. Pat. No. 5,037,638, whose disclosure is incorporated by reference, may have utility in the present invention as part of the monomer portion of the composition.

Still further ingredients such as pigments, tints, stabilizers, surfactants, fluoride release agents and thickening agents may be added to the composition to enhance its stability, color and beneficial properties. For example, well-known LTV absorbers such as Uvinul® 3000 available from BASF Corp. can be present at less than about 0.5 weight percent, and polymerization inhibitors such as hydroquinone monomethyl ether (MEHQ) or 2,6-di-tert-butyl-4-methylphenol (BHT) that can be present at less than 0.1 weight percent, and more usually at less than 0.01 weight percent in the composition. Uvinul® 3000 is preferred as the light stabilizer and MEHQ is preferred as the polymerization inhibitor.

Preferred methods of use of the aforementioned compositions include their use as composite in classic dental restorative procedures such as Class V restorations. Such methods include the usual cleaning and preparation of the tooth surface, followed optionally and preferably by application of a dental adhesive composition, followed by application and curing of the dental compositions indicated above. For example, prepared restorative sites may be pre-treated with dental bonding adhesive systems such as "One Step", "ALL BOND 2" or "ALL BOND 3" from Bisco, Inc., Schaumburg, Ill. according to the manufacturer's instructions. Compositions according to the present invention are then applied to the tooth, preferably by syringe in incremental layers of about 0.5 mm to about 2 mm and cured for about 20–40 seconds (depending on the shade of the composition, darker having higher application times), followed by additional layers and curing until the cavity is completely filled to the cavosurface margin. Any excess material is removed immediately from the surface and the restoration is finished and polished by conventional techniques such as diamonds, discs and polishing pastes. Such finishing also removes any oxygen-inhibited uncured or partially cured layer on the surface of the restoration, which if left in place, might cause staining of the surface over time.

It will also be appreciated by those skilled in the art that the dental compositions and the methods of the present invention have significant utility in other restorative applications. For example, compositions of the invention may also be used as liners in Class I, II, or III restorations. In Class I and II restorations, which typically experience considerable occlusal forces from mastication, use of conventional inflexible, highly filled and hard composites has often led to problems such as creation of marginal gaps. Use of the compositions according to the present invention as liners under such conventional compositions permits their use and avoids such gaps.

Other areas of use of the present inventions which will occur to those of skill in the art include without limitation: use of the compositions under temporary crowns, so-called Class III type restorations, small non-stress Class IV repairs, porcelain veneer bonding, tunnel preparation, splinting, marginal defect repair, deciduous class I or II repair, impart seals, buccal pit restorations, porcelain repair, pit and fissure sealant, adult preventative resin, small core build-up applications, and where maximum strength and polishability is desired.

The following examples are given by way of illustration but without limitation. The preparation of the high molecular weight, multifunctional compounds of the present invention is illustrated in the following example 1. Example 2 describes a preferred formulation of the invention. All parts and percentages are by weight unless otherwise noted.

Compounds identified herein are compounds purchased from the manufactures indicated in the following list, which list also includes the abbreviations used herein to identify those compounds.

| | |
|---|---|
| Acetone | (Ashland Chemical Inc.). |
| CQ | Camphorquinone (Hampford Research, Inc., Stratford, Connecticut). |
| EDMAB | Ethyl dimethylaminobenzoate (Aldrich Chemical Company, Milwaukee, Wisconsin.). |
| ETOH | Ethanol (AAPER Alcohol & Chemical Co.). |
| 2-HEMA | 2-Hydroxyethyl methacrylate (Rohm & Haas Co.). |
| HPMA | Hydroxypropyl methacrylate (Rohm & Haas Co.). |

EXAMPLE 1

Preparation of Compound (X)

4,4'(4,4'-Isopropylidenediphenoxy)-bis(phthalic anhydride) (IBA), 67.75 g (0.13 mole), was ground and weighed into a 250 ml round bottomed flask fitted with a moisture trap, mechanical stirrer, and a thermometer. 2-Hydroxyethyl-methacrylate (HEMA), 61.0 g (0.26 mole) was added together with 2.5% triethylamine, 3.2 g (0.03 moles). The mixture was stirred and heated under nitrogen at 65° C. for six to eight hours, during which time a clear solution resulted. At this time, the infrared spectrum of the product, 4,4'(4,4'-Isopropylidenediphenoxy)-bis(phthalic) dimethacrylate (IDBM), revealed the disappearance of the anhydride absorption bands.

Symmetrical 4,4'(4,4'-Isopropylidenediphenoxy)-bis(phthalic)dimethacrylate (IDBM), 101.6 g (0.13 mole), was weighed into a flask. Glycidyl-methacrylate (GMA), 113.75 g (0.8 mole) was added and the mixture was stirred and heated under nitrogen at 65° C. for six to eight hours, during which time a clear solution resulted. At this time, the infrared spectrum of the product revealed the disappearance of the acid absorption bands.

The symmetrical, tetrafunctional methacrylate product from the above reaction, 138.62 g (0.13 mole), was weighed into a flask. 2-Isocyanoethyl-methacrylate (IEMA), 38.5 g (0.26 mole) was added together with 2.5% DBTDL, 3.2 g (0.03 moles). The mixture was stirred and heated under nitrogen at 65° C. for six to eight hours, during which time a clear solution resulted. At this time, the infrared spectrum of the hexafunctional product revealed the disappearance of the hydroxy absorption bands.

EXAMPLE 2

Preparation of Dental Compositions

Dental compositions were formulated according to the following amounts and procedures.

TABLE 1

Formulation 1

| Component | Weight Percent |
|---|---|
| Hexafunctional Methacrylate Ester | 100 |
| CQ | 0.5 |
| EDMAB | 1.5 |
| Sr Glass (RWG) Porcelain ground | 85 |
| OX-50 | 15 |

A solution of Compound X containing a polymerization initiator system and other compounds was formulated by admixing 100% Compound X with 1.5% EDMAB, 0.5% CQ, 85% Sr Glass (RWG) Porcelain ground, and 15% OX-50. The mixture was protected from light during and after such mixing. The resultant resin compositions exhibited good viscosity and flowability, and were easily dispensable from their syringes. In terms of total weight of the composition, the compositions included total weight percentage of about 15 wt. % Compound X and about 85 wt. % filler.

EXAMPLE 3

Testing of Dental Compositions

The composition of Example 2, comprising 85 wt. % filler and 15 wt. % Compound X was tested for its tensile strength (DTS), compressive strength (CS), Barcol Hardness (935), flexural modulus (FM), water sorption, and cytotoxicity according to the following methods.

1.A. Sample Preparation

A diametral tensile strength (DTS) test specimen of the above-identified composition was prepared by filling a 6 mm diameter and 3 mm deep stainless steel cavity mold. The composition was light-cured for 40 seconds on each side (2×40 sec.) using a 500 milliwatt light source such as an Optilux 400, Demetron Research Corp., Dansbury, Conn.) light source.

Compressive Strength (CS) specimen of the same composition was prepared in a similar manner by filling a 4 mm diameter by 6 mm deep two-piece stainless steel mold followed by light curing on each side for 60 seconds. (2×60 sec.) using the light powered source and intensity indicated for the DTS specimen.

Flexure strength and flexure modulus of the composition were determined by creating a bar-shaped specimen (25 mm×2 mm×2 mm) from a two-piece stainless steel mold. Curing was effected using the same light source and intensity indicated above but applied for 2×40 sec. on one side of the mold.

1.B. Strength and Flexibility Testing

Diametral tensile strength, compressive strength, flexure strength and flexure modulus were measured by loading each specimen to failure on a Model 4466, Instron Corp., Canton, Mass. for DTS and CS tests and on a QTest 4, MTS Systems, Cary, N.C. for the FS and FM tests. Eight specimens were broken for each test, and the results averaged. A croos-head speed of 10 mm/min. was used for compression strength and diametral tensile strength testing, while a cross-head speed of 0.75 mm/min. was used for flexure testing.

Flexure strength measurements are useful in evaluating a material because they involve both tensile and compressive stresses under loading. As the load is applied along the length of the bar-shaped specimen, the side in direct contact with the applied load is subjected to compression, while the opposite parallel side is subjected to tensile forces. Since tooth restorations in the mouth undergo complex stresses, it is of interest to consider tests, which are similar to what occurs naturally. The flexure strength values indicate that the composite becomes more flexible (elastic) as more monomer is added to the resin, although the flexure strength decreases. This increase in elasticity may adversely affect the flexure modulus of a material. Since an increase in elasticity may increased the deflection under a given load, the flexure modulus decreases as the monomer content is added.

1.C. Mixed Mold Fracture Toughness Test Methods

Mixed mode fracture toughness values were obtained from a specimen made from a stainless steel mold (diameter 25 mm and thickness 2 mm) and cured for two minutes on each side (Triad II, Dentsply International Inc., York, Pa.) (3). A chevron notch with an initial crack length of a 0–2 mm was machined in the middle of each specimen using steel blades 20 mm in diameter and 0.75 mm in thickness.

1.D. Results

The forgoing testing yielded the following results:

TABLE 2

Diametral tensile strength (DTS) of formulation 1 after 24 hours in water

| Specimen # | Diameter (cm) | Thickness (cm) | Instron reading (kg) | DTS (Mpa) |
| --- | --- | --- | --- | --- |
| 1 | 0.6 | 0.316 | 151.9 | 50.04 |
| 2 | 0.593 | 0.318 | 161.5 | 53.49 |
| 3 | 0.593 | 0.327 | 174.4 | 56.18 |
| 4 | 0.594 | 0.318 | 151.1 | 49.96 |
| 5 | 0.587 | 0.319 | 161.1 | 53.74 |
| 6 | 0.595 | 0.326 | 152.5 | 49.11 |
| 7 | 0.591 | 0.321 | 163.4 | 53.80 |
| 8 | 0.602 | 0.317 | 164.7 | 53.91 |
| Average | | | 160.1 | 52.53 |
| St. Dev. | | | 7.5 | 2.34 |
| % St. Dev. | | | 4.66 | 4.45 |

TABLE 3

Compressive strength of formulation 1 after 24 hours in water

| Specimen # | Instron reading (kg) | Diameter (cm) | Compressive strength (Mpa) |
| --- | --- | --- | --- |
| 1 | 354 | 0.411 | 261.7 |
| 2 | 345.8 | 0.396 | 275.3 |
| 3 | 359.1 | 0.398 | 283.1 |
| 4 | 367.2 | 0.39 | 301.4 |
| 5 | 321.5 | 0.388 | 266.6 |
| 6 | 328.9 | 0.39 | 270.0 |
| 7 | 327.9 | 0.4 | 255.9 |
| 8 | 302.6 | 0.387 | 252.3 |
| Average | 338.4 | | 270.8 |
| St. Dev. | 21.8 | | 15.9 |

Flexure modulus values were measured immediately after curing on one set of samples, and after curing and subsequent immersion in water at 37 degrees Centigrade for 24 hours.

2. Water Sorption

Water sorption of the composition was also determined according to ANSI/ADA Specification No. 27 (1993) for resin based filler materials. The cured sample exhibited a water sorption of 13 $\mu g/mm^3$.

3. Cytotoxicity Testing

Cytotoxicity of the composition was also studied using the solid agarose overlay method. A monolayer of L-929 mouse fibroblast cells was grown to confluency in the presence of 5% $CO_2$ and overlaid with double strength Minimum Essential Medium supplemented with 10% serum and 4% antibiotics (2×MEM), supplemented with neutral red and 2% agarose. A 1 cm×1 cm portion of the test article, a 1.0 cm length piece of high density polyethylene as a negative control, and a 1.0 cm by 1.0 cm piece of tin stabilized polyvinylchloride as a positive control were each placed on the solidified agarose surface in a cell culture well. The wells were labeled and incubated at 37° C. in 5% $CO_2$ for 24 hours. Following incubation, the cultures were examined macroscopically for cell decolorization and to determine the zone of cell lysis (if any). The cell monolayers were examined microscopically to verify any decolorized zones and to determine cell morphology in proximity to the articles. The results are shown in Table 4 and scored as follows:

Nontoxic (N): Normal cell morphology in proximity to the sample.

Toxic (T): Cellular death and degeneration associated with the area beneath the sample and possibly extended beyond the perimeter of the sample. Where a zone of lysis was observed, the distance from the edge of the sample to the edge of the zone was measured and reported in millimeters (mm).

TABLE 4

| Articles | Score | Zone of Lysis (mm) |
| --- | --- | --- |
| Hard Resin Disk of Formulation 1 | N | 0 |
| Negative Control | N | 0 |
| Positive Control | T | 6 |

Under the conditions of this study, the test article showed no evidence of causing cell lysis or toxicity. The test article would not be considered toxic to L-929 mouse fibroblast cells. The negative control and the positive control performed as anticipated.

4. Testing for the Polymerization Volumetric Shrinkage Measurements of Composite Samples The AcuVoITM (BISCO, Inc.) was initiated and the surface of the pedestal was wiped with Kimwipes to remove any debris until volume reads as zero. About 10 to 15 mg of the composite was put on the pedestal in a semi-spherical shape, the height of which was 2 mm or less and the width of which was smaller than the pedestal. A VIPTM light gun (Bisco, Inc.) was put on the holder and placed about 2 mm from the sample and adjusted so that the metal tip from VIPTM gun didn't reflect any light or shade any background light. The appearance of the sample and the shrinkage value was checked to make sure that it read in the range of 0.00 to 0.04%. The brightness value was adjusted to make sure the object was not shaded or fizzy. When the volume readings were stable, the sample was completely cured and the conditions were recorded (e.g., VIP, 40 seconds, and 500 n W/cm2), making sure that the gun position was not changed during the curing process. The sample was allowed to completely cool and settle. When the volume readings stabilized, (about five minutes) the shrinkage and the time were recorded (e.g., 5 minutes after the cure, 3.05%). Measurements were repeated until the measured shrinkage deviations didn't exceed +0.05% (e.g., three readings of 2.05, 2.10, and 2.00%).

5. Testing the Strain of a Ring Encircling a Curing Composite and Calculating the Polymerization Contraction Stress Strain measurements and stress calculations are properties representing the stress that a curing composite may produce on the restored tooth. Their magnitudes depend on the final elastic modulus, shrinkage, curing rate and configuration of the curing composite as well as the modulus and configuration of the ring. While acrylic rings are more sensitive to the shrinkage of the composite aluminum rings are sensitive to its modulus. Generally speaking, acrylic rings are easier to use and the data are more consistent but they cannot usually be used to compare different composites. Aluminum rings, on the other hand, tend to produce strain (stress) data that make more sense, which at least follows the trend measured by other techniques. Aluminum rings, however are difficult to use, very technique dependent, and may not apply to some de-bonding prone composites. For these strain measurements a 3800 Strain Indicator with Model 2000 A/D Converter (Measurements Group, Raleigh, N.C.) with strain gages (EA-13-062AP-120 or EA-06-062AP-120) with an optional computer controlled power supply, BPD 15–20 was used. Acrylic rings were prepared by cutting acrylic tubing of 9.6 mm OD and 6.3 mm ID (⅜" and ¼") into a 2.0 mm thick ring using an Isomet diamond saw (4 turns+5 divisions on the micrometer positioner). The inner walls were roughened with 3000 grit sand paper and coated with two coats of One-Step. After 30s, the coating was light cured for 10s at 500 MW/CM2—If debonding occurred, another One-Step coating is applied on the cured layer without curing. One can prepare several rings at once and can store the rings in the dark for up to 3 days. Aluminum rings were prepared by cutting aluminum tubing of 9.6 mm OD and 6.3 mm ID (⅜" and ¼') into a 2.0 mm thick ring using the Isomet diamond saw (4 turns–5 divisions on the micrometer positioner). The inner wall were sandblasted with alumina powders and coated twice with All Bond 2 (blend of A and B). After 60 seconds, the coating was light cured for 20 seconds at 500 mW/cm$^2$ and used within 60 minutes. A strain gage was prepared by clamping it on a board, shiny face up, and cutting the gage into a smaller dimension with a sharp blade without cutting it beyond the dots outside of the metal grid. The gage's leads were connected onto the ports of the strain indicator: red to red, white to white, and black to yellow with D120. The light intensity, indicator, and software readings were calibrated (if necessary) and the irradiation profile (intensity and duration) was set up by adjusting the distance between the bottom of the tip and the top of a ring to be the same as what was used for intensity calibration. A strain gage was attached to a ring by brushing a thin layer of blue catalyst onto the back of the gage and letting it dry for 60 s. Double stick tape was adhered to an edge of a lab jack. If the ring is aluminum, 1500 grit paper is used to clear the outer wall where the gage is to be glued. If the ring is acrylic, the ellipticity is checked. The ring is adhered vertically on the double stick tape (with the major axis horizontally oriented if the ring is acrylic) and transparent tape is adhered onto the top of gage, opposite to the catalyst. A thin layer of adhesive is brushed on the top of outer wall and the gage is aligned with the ring and pressed onto the wall of the ring holding it for 20 seconds for acrylic and 30 seconds for aluminum rings. After 30 seconds, the decreasing reading indicates the curing of the adhesive. After curing, the tape is removed from the gage.

The sample is loaded into an acrylic ring by pressing the gage horizontally on the double stick tape with the gage off the edge of the jack. A small amount (less than ½) of composite is added into the ring and the bottom is filled, taking special care to fill and pack the edges of the composite well so that there are no visible voids between the wall and the composite without overflowing. Overflow of less than 0.5 mm thick is not removed, however, overflow above this amount must be removed and the remaining composite repacked to get rid of any gaps. The composite is then immediately cured.

The sample is loaded into an aluminum ring by coating a thin film of Pre-Bond on top of the ALL Bond 2 before pressing the gage horizontally on the double stick tape with the gage off the edge of the jack. A small amount (less than ½) of composite is added into the ring and the bottom is filled, taking special care to fill and pack the edges of the composite well so that there are no visible voids between the wall and the composite without overflowing. Overflow of less than 0.5 mm thick is not removed, however, overflow above this amount must be removed and the remaining composite repacked to get rid of any gaps. The ring is covered to shield any ambient light and allowed to sit for 20 min before the composite is cured. The gage is carefully peeled off for the next measurement and the sample is removed. The following equations can be used to convert the measured micro-strain ($\epsilon$) into stress ($\sigma$):

$$\sigma(Mpa)=2.0\times10^{-3}\epsilon(\mu m/m) \text{ for acrylic rings (Young's modulus equals 3.0 Gpa)}$$

$$\sigma(Mpa)=47\times10^{-3}\epsilon(\mu m/m) \text{ for aluminum rings (Young's modulus equals 70 Gpa)}$$

By using the formulation of the present invention, a much lower (2% or less by volume fraction) shrinkage is obtained in the resulting composite as compared with commercial universal hybrid composites, which shrink from 2.2 to 3.5% by volume fraction (see Table 5). The above test values also demonstrate that the composition exhibited good flexibility, tensile strengths and Barcol hardness. Very low modulus of flexibility were observed for the composition, i.e. only about 2 GPa immediately after curing, and only about 3 GPa after 24 hours immersion in water at physiological temperature. As can also be seen below in Table 5, such values are well below those for conventional filled composites. Those low modulus values for the composition, considered along with its good flexibility and tensile strength and water sorption, indicate that the composition is well suited as a restorative material in Class I, II, IV, V restorations and core build-ups and other applications involving shear and tensile stresses, and can dissipate those as well as internal shrinkage-induced polymerization stresses. An almost 4-fold lower contraction stress was found in the invented composite under light cure in comparison with commercial hybrid composites (see Table 5). A lower contraction stress will dramatically reduce the risk of microleakage in the tooth/restoration surface.

TABLE 5

A Comparison for Volumetric Shrinkage and Microstrain of a Low Shrinkage Composite and Commercial Composites

| Composites | Low Shrinkage | Z100 | Herculite | Heliomolar | TPH Spectrum |
|---|---|---|---|---|---|
| Shrinkage Vol % | 0.9–1.3 ± 0.02 | 2.7 ± 0.1 | 2.9 ± 0.1 | 2.2 ± 0.1 | 3.6 ± 1 |
| Microstrain μm/in | 479–950 | 1730 ± 30 | 1400 ± 90 | 730 ± 50 | 1420 ± 60 |

The foregoing detailed description has been given for clearness of understanding only, and no unnecessary limitations should be understood therefrom, as modifications will be obvious to those skilled in the art.

What is claimed is:

1. A compound having the formula:

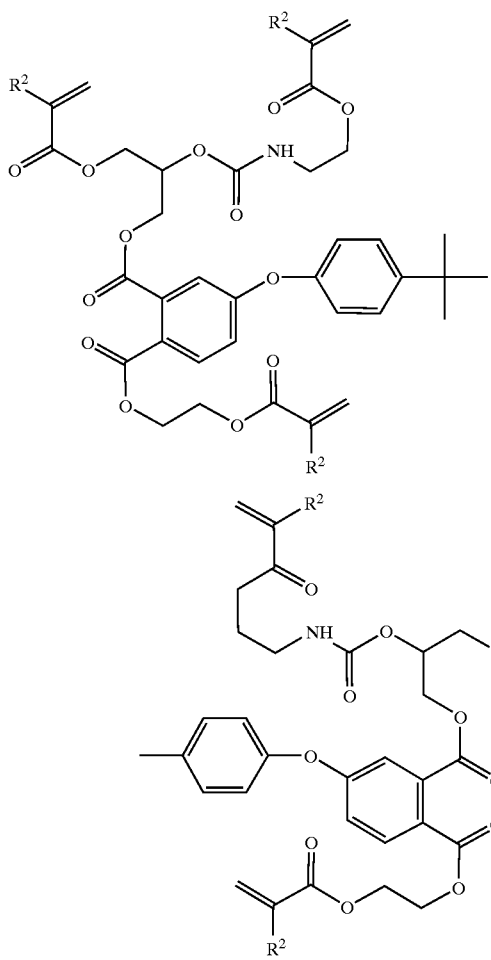

wherein $R^2$ is H or $CH_3$.

2. The compound of claim 1, wherein $R^2$ is $CH_3$.

3. A method of making a compound having the formula

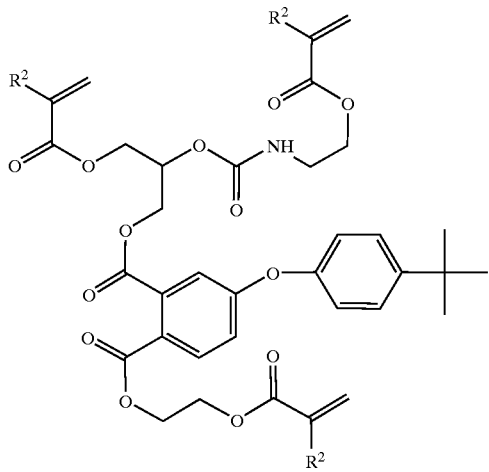

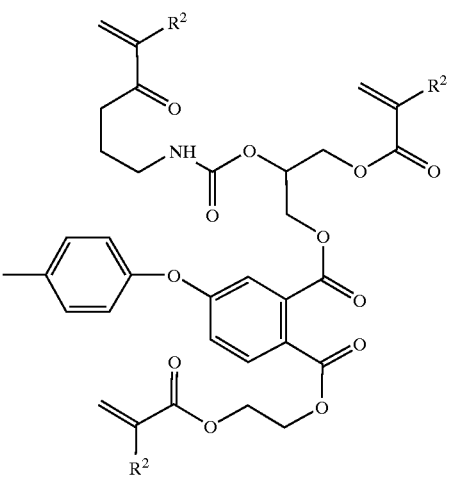

wherein $R^2$ is H or $CH_3$, the method comprising:

(a) contacting a cyclic anhydride having the formula:

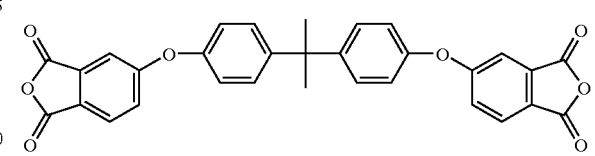

with an ethylenically unsaturated alcohol having 3 to 12 carbon atoms having the formula:

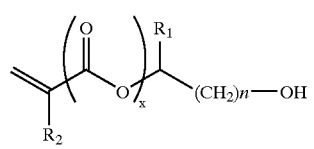

wherein $R^1$ is H, $CH_3$, or $=CH_2$; $R^2$ is H or $CH_3$; n is 1, 2, 3, or 4; and x is 0 or 1;

(b) contacting the product of step (a) with an ethylenically unsaturated glycidyl ether having 3 to 12 carbon atoms having the formula:

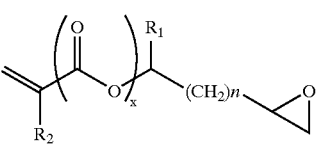

(c) contacting the product of step (b) with an ethylenically unsaturated isocyanate having 3 to 12 carbon atoms having the formula:

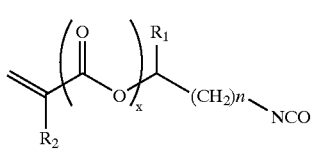

4. The method of claim 3, wherein the ethylenically unsaturated alcohol having 3 to 12 carbon atoms is 2-hydroxyethyl methacrylate.

5. The method of claim 3, wherein the ethylenically unsaturated glycidyl ether is glycidyl methacrylate.

6. The method of claim 3, wherein the ethylenically unsaturated isocyanate is 2-isocyanoethyl methacrylate.

7. A primer for improving the bond strength between a dental composite and dentin or a metal selected from the group consisting of barium, strontium, and zirconium, the primer comprising the compound of claim 1.

8. A dental composite comprising the compound of claim 1.

9. A method for improving the bond strength between a dental composite and dentin or a metal selected from the group consisting of barium, strontium, and zirconium, the method comprising applying to the surface of the dentin or the metal an effective quantity of a primer in accordance with claim 7 before the application of the dental composite thereto.

* * * * *